United States Patent [19]
Keenan

[11] Patent Number: 5,869,505
[45] Date of Patent: *Feb. 9, 1999

[54] NICOTINE METABOLITES AND NICOTINE DEPENDENCE

[76] Inventor: Robert M. Keenan, 2901 Boston St. #209, Baltimore, Md. 21224

[*] Notice: The term of this patent shall not extend beyond the expiration date of Pat. Nos. 5,573,774 and 5,596,007.

[21] Appl. No.: 12,379

[22] Filed: Feb. 2, 1993

[51] Int. Cl.⁶ .................................................. A61K 31/44
[52] U.S. Cl. .......................................... 514/343; 514/813
[58] Field of Search ..................................... 514/343, 813

[56] References Cited

U.S. PATENT DOCUMENTS

| | | |
|---|---|---|
| 3,048,520 | 7/1962 | McKennis et al. . |
| 3,867,519 | 2/1975 | Michaels . |
| 3,870,791 | 3/1975 | Haddad et al. . |
| 3,870,794 | 3/1975 | Hutchinson et al. . |
| 4,051,842 | 10/1977 | Hazel et al. . |
| 4,136,177 | 1/1979 | Lin et al. . |
| 4,140,122 | 2/1979 | Kuhl et al. . |
| 4,255,415 | 3/1981 | Chrai et al. . |
| 4,383,529 | 5/1983 | Webster . |
| 4,621,074 | 11/1986 | Bourne . |
| 4,668,506 | 5/1987 | Bawa . |
| 4,713,244 | 12/1987 | Bawa et al. . |
| 4,748,181 | 5/1988 | Hutchinson et al. .................... 514/343 |
| 4,788,063 | 11/1988 | Fisher et al. . . |
| 4,835,162 | 5/1989 | Abood .................................... 514/305 |
| 4,931,279 | 6/1990 | Bawa et al. . |
| 4,946,853 | 8/1990 | Bannon et al. .......................... 514/343 |
| 4,966,916 | 10/1990 | Abood .................................... 514/534 |
| 5,278,176 | 1/1994 | Lin ......................................... 514/343 |

OTHER PUBLICATIONS

R. Barbieri et al, "Nicotine, Cotinine and Anabasine Inhibit Aromatase in Human Trophoblast in Vitro", *J. Clin. J. Steroid Invest.*,77:17271733 (1986).

R. Barbieri et al, "Nicotine, Cotinine and Anabasine on Rat Adrenal 11B–hydroxylase and 21–hydroxylase". *J. Steroid Biochem.*,28: 25–28 (1987).

R. Barbieri, et al, "Cotinine and Nicotine Inhibit Human Fetal Adrenal 11B–hydroxylase", *Journal of Clinical Endocrinology and Metabolism*, 69 :1221–1224 (1989).

N. Benowitz et al,"Cotinine Disposition and Effects", *Clin. Pharmacol. Ther.,*, 34 :604–611 (1983).

N. Benowitz et al,"Inverse Relation Between Serum Cotinine Concentration and Blood Pressure in Cigarette Smokers", *Circulation*, 80:1309–1312 (1989).

J. Borzelleca et al,"Studies on the Respiratory and Cardiovascular Effects of (–) —Cotinine",*J. Pharm. Exper. Therapeutics*, 137 :313–318 (1962).

E. Bowman et al,"(–) —Cotinine", *Biochemical Preparations*, 10:36–39 (1963).

E. Bowman et al,"Disposition and Fate of (–)—Cotinine in the Mouse", *The Journal of Pharmacology and Experimental Therapeutics*, 143:301–308 (1963).

E. Bowman et al,"Studies on the Metabolism of (–) –Cotinine in the Human ",*J. Pharmacol. Exp. Ther.,*135:306–311 (1962).

R. Chahine et al,"The in Vitro Effects of Nicotine and Cotinine on Prostacyclin and Thromboxane Biosynthesis", *Prostaglandins, Leukotrienes, and Essential Fatty Acids*, 40: 261–266 (1990).

M. Curvall et al,"Simulation and Evaluation of Nicotine Intake During Passive Smoking: Cotinine Measurements in Body Fluids of Nonsmokers Given Intravenous Infusions of Nicotine", *Clinical Pharmacol Therapy*, 47:42–49 (1990).

M. Curvall et al,"The Pharmacokinetics of Cotinine in Plasma and Saliva from Non–Smoking Healthy Volunteers", *The European Journal of Clinical Pharmacology*, 38:281–287 (1990).

E. Di Giusto et al,"Kinetics of Cotinine After Oral and Intravenous Administration to Man", *The European Journal of Clinical Pharamacology*,31:583588 (1987).

P. DeSchepper et al,"Kinetics of Cotinine After Oral and Intravenous Administration to Man", *The European Journal of Clinical Pharmacology*, 31:583–588 (1987).

J. Gabrielsson et al,, "Constant–Rate Infusion of Nicotine and Cotinine. I. A Physiological Pharmacokinetic Analysis of the Cotinine Disposition, and Effects on Clearance and Distribution in the Rat", *The Journal of Pharmacokinetics and Biopharmaceutics*, 15:583–599 (1987).

E. Di Giusto et al, "Some Properties of Saliva Cotinine Measurements in Indicating Exposure3 to Tobacco Smoking", *The American Journal of Public Health*, 76:1245–1246 (1986).

D Glenn et al, "Synthesis and Mass Spectrometry of Some Structurally Related Nicotinoids", *The Journal of Organic Chemistry*, 43:2860–2870 (1978).

S. Goldberg et al, "Nicotine and Some Related Compounds: Effects on Schedule–Controlled Behavior and Discriminative Properties in Rats", *Psychopharmacology*, 97:295–302 (1989).

J. Idle, "Titrating Exposure to Tobacco Smoke Using Cotinine–A Minefield of Misunderstanding", *The Journal of Clinical Epidemiol*, 43:313–317 (1990).

P. Jacob et al, "Disposition Kinetics of Nicotine and Cotinine Enantiomers in Rabbits and Beagle Dogs", *The Journal of Pharmaceutical Sciences*, 77:396–400 (1988).

L. Jarczyk et al, "Serum and Saliva Concentrations of Cotinine in Smokers and Passive Smokers", *The Journal of Clinical Chemical Biochemistry*, 27:230–231 (1989).

(List continued on next page.)

*Primary Examiner*—Marianne M. Cintins
*Assistant Examiner*—M. Moezie
*Attorney, Agent, or Firm*—Burd, Bartz & Gutenkauf

[57] ABSTRACT

A therapeutic method is provided to alleviate the tobacco withdrawal syndrome, the symptoms of nicotine withdrawal or the management of human body weight in nicotine-experienced or nicotine-naive individuals, comprising of administering an amount of nicotine metabolites or a pharmaceutically acceptable salts thereof to a human in need of such treatment, in an amount which is effective to reduce or eliminate at least one of the symptoms of the tobacco withdrawal syndrome, nicotine withdrawal or manage human body weight.

59 Claims, No Drawings

OTHER PUBLICATIONS

M. Jarvis et al, "Biochemical Markers of Smoke Absorпортion and Self Reported Exposure to Passive Smoking", *The Journal of Epidemiology and Community Health*, 38:335–339 (1984).

J. Jordanov, "Cotinine Concentrations in Amniotic Fluid and Urine of Smoking, Passive Smoking and Non–Smoking Pregnant Women at Term and in the Urine of Their Neonates on 1st Day of Life", *The European Journal of Pediatrics*, 149:734–737 (1990).

K., Kim et al, "Effects of Some Nicotine Metabolites and Related Compounds on Isolated Smooth Muscle", *The Journal of Pharmacology and Experimental Therpeutics*, 161:59–69 (1968).

B. Kuo et al, "Influence of Nicotine and Cotinine on the Expression of Plasminogen Activator Activity in Bovine Aortic Endothelial Cells", *Thrombosis and Haemostasis*, 61:70–76 (1989).

G. Kyerematen et al, "Disposition of Nicotine and Eight Metabolites in Smokers and Nonsmokers: Identification in Smokers of Two Metabolites That are Longer Lived Than Nicotine", *Clinical Pharmacol Ther.*, 48:641–651 (1990).

W. Luck et al, "Extent of Nicotine and Cotinine Transfer to the Human Fetus, Placenta and Amniotic Fluid of Smoking Mothers", *Dev. Pharmacol. Ther.*, 8:384—395 (1985).

C. Lynch et al, "Spontaneous Cigarette Brand Switching: Consequences for Nicotine and Carbon Monoxide Exposure", *The American Journal of Public Health*, 78:1191–1194 (1987).

H. McKennis et al, "Alternate Routes in the Metabolic Degradation of the Pyrrolidine Ring of Nicotine", *The Journal of Biological Chemistry*, 239:3990–3996 (1964).

A. Meikle et al, "Nicotine and Cotinine Effects on 3 Alpha Hydroxysteroid Dehydrogenase in Canine Prostate", *Life Sciences*, 43:1845–1850 (1988).

A. McNeill et al, "Saliva Cotinine as an Indicator of Cigarette Smoking in Adolescents ", *The British Journal of Addiction*, 82:1355–1360 (1987).

M. Noland et al, "Saliva Cotinine and Thiocyanate: Chemical Indicators of Smokeless Tobacco and Cigarette Use in Adolecents", *The Journal of Behavioral Medicine*, 11:423–433 (1988).

M. Risner et al, "Effects of Nicotine, Cocaine and some of Thier Metabolites on Schedule–Controlled Responding by Beagle Dogs and Squirrel Monkeys", *The Journal of Pharmacology and Experimental Therpeutics*, 234:113–119 (1985).

G. Scherer et al, "Pharmacokinetics of Nicotine, Cotinine and 3'–Hydroxycotinine in Cigarette Smokers", *Klin Wochenschr*, 66: 5–11 (1988).

S. Schwartz et al, "Studies on the Degradation of the Pyrrolidine Ring of (–) –Nicotine in Vivo", *The Journal of Biological Chemistry*, 238:1807–1812 (1963).

D. Sepkovic et al, "Biomedical Applications of Cotinine Quantitation in Smoking Related Research", *Public Health Briefs, The American Journal of Public Health,* 75:663–665 (1985).

A Report of the Surgeon General, "The Health Consequences of Smoking –Nicotine Addiction", 197–208 (1988), U. S. Department of Health and Human Services.

B. Testa et al, "Circular Dichroic Determination of the Preferred Conformation of Nicotine and Related Chiral Alkaloids in Aqueous Solution", *Molecular Pharmacology*, 9:10–16 (1973).

S. Thompson et al, "Relation of Urinary Cotinine Concentrations to Cigarette Smoking and to Exposure to Other People's Smoke", *Thorax*, 45:356–361 (1990).

H. Van Vunakis et al,Decreased Serum Cotinine Levels in Smokers of Both Tobacco and Marijuana as Compared With Smokers of Tobacco Only, *Pharmacology Biochemistry & Behavior*, 30:895–898 (1988).

L. Wagenknecht et al, "Racial Differences in Serum Cotinine Levels Among Smokers in the Coronary Artery Risk Development in (Young) Adults Study", *The American Journal of Public Health*, 80:1053–1056 (1990).

K. Yomamoto et al, "Nicotine–Induced Eeg and Behavioral Arousal", *Int. J. Neuropharmacol*, 4:359–373 (1965).

J. Yeh et al, "Nicotine and Cotinine Inhibit Rat Testis Androgen Biosnythesis in Vitro", *J. Steroid Biochem*, 33:627–630 (1989).

Rylander et al., "Exposure to Environmental Tobacco Smoke . . . ", Acta Poediatr Scand, vol. 78: 449–50 (1989).

Sasson et al., "Cigarette Smoking and Neoplasia of the Uterine Cervix . . . "The New England Journal of Medicine, 312:315–316 (1985).

Galeazzi et al., "Steady–State Concentration of Cotinine . . .", European Journal of Clinical Pharmacology, vol. 28: 301–304 (1985).

5,869,505

NICOTINE METABOLITES AND NICOTINE DEPENDENCE

FIELD OF THE INVENTION

The invention relates to the therapeutic methods and articles of manufacture to alleviate the tobacco withdrawal syndrome or manage human body weight with the use of nicotine metabolites or pharmaceutically acceptable salts thereof. The invention includes methods and articles of manufacture using nicotine metabolites or pharmaceutically acceptable salts thereof to alleviate symptoms of nicotine withdrawal and craving associated with cessation of tobacco or nicotine use, as well as the management of human body weight in nicotine-experienced or nicotine-naive humans.

BACKGROUND OF THE INVENTION

Cigarette smoking continues to be the major preventable cause of death in the United States resulting in nearly 400,000 deaths per year due to cancer and cardiovascular disease. Despite the potential adverse health effects, the vast majority of cigarette smokers are unable to cease smoking. The lack of smoking cessation success is thought to be related to the tobacco withdrawal syndrome or tobacco abstinence syndrome that most smokers experience during their attempts to quit. See, Office of Smoking and Health, *The Health Consequences of Smoking: Nicotine Addiction. A Report to the Surgeon General*, U.S. Govt. Print. Off., Washington D.C., DHHS Pub. No. (CDC) 88–8406 (1988). The most common effects are similar to those in almost all abstinence syndromes, and include decreased heart rate, anxiety, tension, difficulty concentrating, impatience, depression, increased appetite with accompanied weight gain, irritability and restlessness. See, American Psychiatric Assoc., *Diagnostic and Statistical Manual*, Washington D.C. (3rd ed. 1980) at pages 159–160, 176–178. Most withdrawal effects occur within 24 hours, peak in the first 1–2 weeks and significantly decrease at one month. It is widely believed that the effects of abstinence from tobacco are due to nicotine deprivation, and that abstinence effects from smoking prevent smokers from stopping. See, J. R. Hughes et al., in *Research and Advances in Alcohol and Drug Problems*, Vol. 10, L. T. Kozlowski et al., eds., Plenum Pub. Corp. (1990) at pages 317–398.

The relationship between tobacco use and decreased body weight has been known for more than 100 years. It has been well established that smokers weigh less than non-smokers. Recent research has shown that nicotine is the substance responsible for the decreased body weight of tobacco users (See, Chapter on Nicotine Dependence, The National Institute On Drug Abuse's Fourth Triennial Report to Congress, In Press). Two major factors related to nicotine use cessation are responsible for weight gain in the post-tobacco cessation period including 1) decreased metabolism and/or 2) increased dietary intake. Conversely, it must be the case that nicotine use results in increased metabolism and/or decreased dietary intake.

In an attempt to reduce post-cessation weight gain and achieve long-term tobacco cessation success, the effects of nicotine replacement (nicotine gum) on post-cessation weight gain were examined over a ten week post-cessation period. Nicotine gum when compared to placebo was shown to reduce the weight gained in the post-cessation period by approximately 50 percent (3.8 versus 7.8 pounds, respectively), and the magnitude of this beneficial effect was related to the amount of nicotine gum used. Similarly, it was found that nicotine gum use by abstinent cigarette smokers reduced the frequency and severity of self-reported "Hunger" scores and self-reported eating over the first month of nicotine abstinence. Increases in self-reported measures of hunger are likely related to increased weight gain in the post-cessation period (See, chapter on Nicotine Dependence, The National Institute On Drug Abuse's Fourth Triennial Report to Congress, In Press). As a result of the above findings, the use of an appetite suppressant, therefore, should prevent post-cessation weight gain in nicotine-experienced individuals.

Of the pharmacological approaches to aiding tobacco use cessation, nicotine replacement, e.g., via transdermal nicotine patches or nicotine gum, is the most widely used. Nicotine gum decreases abstinence discomfort, especially anxiety, decreased memory and irritability. On the other hand, nicotine gum does not reliably decrease weight gain or craving. Also, discontinuing use of nicotine gum leads to some of the same symptoms as the cigarette withdrawal syndrome. Furthermore, nicotine is toxic, and the availability of nicotine gum or patches poses a risk of poisoning to children and pets.

Other studies have demonstrated that alpha-2 agonists, such as clonidine, decrease postcessation anxiety, irritability and difficulty concentrating. Decreased sympathetic activity has been postulated to be the mechanism by which these drugs decrease abstinence effects. Although tobacco abstinence has some effects that could be attributed to sympathetic activity, it lacks the typical signs and symptoms of sympathetic overactivity, such as tachycardia, diaphoresis and hypertension. Thus, the mechanism by which alpha-2 agonists exert their effects is unclear. While a number of other pharmacological treatments, such as use of doxepin, ACTH, and corticotrophins, for abstinence symptoms have been tested, none of the studies reported baseline and postcessation values for abstinence symptoms. See, for example, S. J. Bourne (U.S. Pat. No. 4,621,074).

Therefore, a continuing need exists for pharmacological treatments that will facilitate smoking cessation, e.g., by blocking or relieving tobacco withdrawal syndrome, or reducing the symptoms of nicotine withdrawal. Also, a weight management agent should prove useful as a tool to assist the tobacco user in their cessation attempt.

SUMMARY OF THE INVENTION

The present invention provides a therapeutic method of treatment to (a) alleviate tobacco withdrawal syndrome (TWS), (b) alleviate the similar abstinence effects due to cessation of nicotine alone, or (c) manage body weight in nicotine-experienced or nicotine-naive individuals comprising of administering to a human in need of such treatment, i.e., a nicotine user, abstinent nicotine user or nicotine-naive, an amount of a nicotine metabolite or a combination of nicotine metabolites (e.g., cotinine, nornicotine, norcotinine, nicotine N-oxide, cotinine N-oxide, 3-hydroxycotinine, 5-hydroxycotinine) or their pharmaceutically acceptable salts thereof, in an amount effective to significantly reduce or eliminate at least one of the symptoms of TWS or nicotine withdrawal. As discussed above, the symptoms of both tobacco and nicotine withdrawal are similar and are art recognized to include craving for tobacco, anxiety, irritability, insomnia, impatience, tension, depression, increased appetite with accompanying weight gain, restlessness, difficulty concentrating, drowsiness and decreased heart rate. The present method is effective both to alleviate TWC acutely and to permit patients to maintain abstinence from tobacco use for extended periods of time.

In a preferred embodiment, the present invention also provides a therapeutic method to alleviate the craving for cigarettes, tobacco and/or nicotine that is associated with cessation of nicotine use, e.g., by chewing or smoking, by the administration of an effective amount of a nicotine metabolite or a combination of nicotine metabolites or their pharmaceutically acceptable salts thereof, to a human in need of such treatment. However, the present invention is also useful to treat the symptoms of nicotine withdrawal which are due, for example, to cessation of use of nicotine gum or a nicotine transdermal patch. In addition, this invention should be useful in the management of human body weight in nicotine-experienced or nicotine-naive individuals.

The present invention is exemplified by a study in which a nicotine metabolite, (−)-cotinine base, was intravenously administered to abstinent cigarette smokers. The administration of the nicotine metabolite, cotinine, caused many subjective changes without affecting cardiovascular activity. While cotinine administration appeared to mildly exacerbate some of the symptoms of the tobacco withdrawal syndrome such as anxiety, tension, restlessness and insomnia, it simultaneously decreased ratings of sedation and hunger. Also, cotinine administration reduced peak craving scores for cigarettes, tobacco and/or nicotine experienced during the session.

Nicotine metabolites may have many qualities which can enhance their value as aids to smoking cessation. In particular, cotinine has a long in vivo half-life, no cardiovascular activity, complete oral bioavailability, potentially low abuse liability and has not been reported to be harmful even at very high doses in many species including man. Also, because cotinine has no significant cardiovascular effect, a combined pharmacologic replacement treatment approach using cotinine in combination with nicotine or other metabolites of nicotine may be possible. The other nicotine metabolites should have many of these same qualities, and therefore should provide relief from the aforementioned problems in a similar manner.

The present invention also provides an article of manufacture comprising packaging material, such as a box, bottle, tube, sprayer, insufflator, intravenous (i.v.) bag, envelope and the like; and at least one unit dosage form of a pharmaceutical agent contained within said packaging material, wherein said pharmaceutical agent comprises a nicotine metabolite or combination of nicotine metabolites or their pharmaceutically acceptable salts thereof in an amount effective to alleviate tobacco withdrawal syndrome, the symptoms of nicotine withdrawal or the craving associated with cessation of tobacco smoking or manage human body weight, and wherein said packaging material includes instruction means which indicate that said nicotine metabolite or combination of nicotine metabolites or said pharmaceutically acceptable salts thereof can be used for alleviating tobacco withdrawal syndrome, the symptoms of nicotine withdrawal, the craving associated with the cessation of tobacco smoking or manage human body weight. Suitable instruction means include printed labels, printed package inserts, tags, cassette tapes, and the like.

DETAILED DESCRIPTION OF THE INVENTION

Cotinine

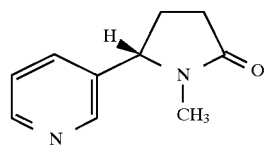

Cotinine has the molecular structure shown above;

The physiologically active form is the (−)-isomer, so as used herein, the term "cotinine" includes (−)-cotinine, or the racemic form, (+/−)-cotinine. The free base, depicted above, can be employed in the practice of the invention, as can the pharmaceutically acceptable salts. These include the amine-acid addition salts of nontoxic organic acids or inorganic acids, such as the tartarate, fumarate ("scotine"), citrate, maleate, malate, hydrobromide, hydrochloride, sulfate, phosphate and the like. For example, see F. Vaitekunas, *J. Amer. Chem. Soc.,* 79, 149 (1957). E. R. Bowman et al., in *J. Pharmacol. Exp. Ther.,* 135, 306 (1962) report the preparation of (−)-cotinine free base from (−)-nicotine. The preparation and purification of (−)-cotinine fumarate is described by N. L. Benowitz et al., *Clin. Pharmacol. Ther.,* 34, 604 (1983). Also, see P. Jacob III, et al., in *Pharmacol. Biochem. Behav.,* 30, 249 (1988) for an explanation of the metabolic pathways of nicotine and the formation of this metabolic product are discussed.

Nornicotine

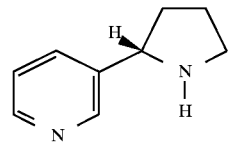

Nornicotine has the molecular structure shown above;

The physiologically active form is the (−)-isomer, so as used herein, the term "nornicotine" includes (−)-nornicotine, or the racemic form, (+/−)-nornicotine. The free base, depicted above, can be employed in the practice of the invention, as can the pharmaceutically acceptable salts. These include the amine-acid addition salts of nontoxic organic acids or inorganic acids, such as the tartarate, fumarate, citrate, maleate, malate, hydrobromide, hydrochloride, sulfate, phosphate and the like. For example, see P. Jacob III, et al., in *Pharmacol. Biochem. Behav.,* 30, 249 (1988) for an explanation of the metabolic pathways of nicotine and the formation of this metabolic product are discussed.

Norcotinine

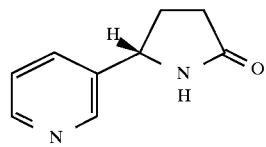

Norcotinine has the molecular structure shown above;

The physiologically active form is the (−)-isomer, so as used herein, the term "norcotinine" includes (−)-norcotinine, or the racemic form, (+/−)-norcotinine. The free base, depicted above, can be employed in the practice of the invention, as can the pharmaceutically acceptable salts. These include the amine-acid addition salts of nontoxic organic acids or inorganic acids, such as the tartarate, fumarate, citrate, maleate, malate, hydrobromide, hydrochloride, sulfate, phosphate and the like. For example, see P. Jacob III, et al., in *Pharmacol. Biochem. Behav.*, 30, 249 (1988) for an explanation of the metabolic pathways of nicotine and the formation of this metabolic product are discussed.

Nicotine N-Oxide

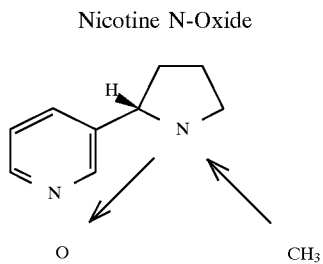

Nicotine N-oxide has the molecular structure shown above;

The physiologically active form is the (−)-isomer, so as used herein, the term "nicotine N-oxide" includes (−)-nicotine N-oxide, or the racemic form, (+/−)-nicotine N-oxide. The free base, depicted above, can be employed in the practice of the invention, as can the pharmaceutically acceptable salts. These include the amine-acid addition salts of nontoxic organic acids or inorganic acids, such as the tartarate, fumarate, citrate, maleate, malate, hydrobromide, hydrochloride, sulfate, phosphate and the like. For example, see P. Jacob III, et al., in *Pharmacol. Biochem. Behav.*, 30, 249 (1988) for an explanation of the metabolic pathways of nicotine and the formation of this metabolic product are discussed.

Cotinine N-Oxide

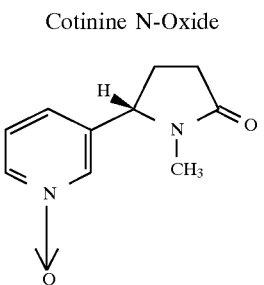

Cotinine N-oxide has the molecular structure shown above;

The physiologically active form is the (−)-isomer, so as used herein, the term "cotinine N-oxide" includes (−)-cotinine N-oxide, or the racemic form, (+/−)-cotinine N-oxide. The free base, depicted above, can be employed in the practice of the invention, as can the pharmaceutically acceptable salts. These include the amine-acid addition salts of nontoxic organic acids or inorganic acids, such as the tartarate, fumarate, citrate, maleate, malate, hydrobromide, hydrochloride, sulfate, phosphate and the like. For example, see P. Jacob III, et al., in *Pharmacol. Biochem. Behav.*, 30, 249 (1988) for an explanation of the metabolic pathways of nicotine and the formation of this metabolic product are discussed.

3-Hydroxycotinine

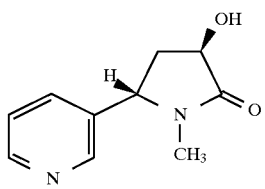

3-Hydroxycotinine has the molecular structure shown above;

The physiologically active form is the (−)-isomer, so as used herein, the term "3-hydroxycotinine" includes (−)-3-hydroxycotinine, or the racemic form, (+/−)-3-hydroxycotinine. The free base, depicted above, can be employed in the practice of the invention, as can the pharmaceutically acceptable salts. These include the amine-acid addition salts of nontoxic organic acids or inorganic acids, such as the tartarate, fumarate, citrate, maleate, malate, hydrobromide, hydrochloride, sulfate, phosphate and the like. For example, see P. Jacob III, et al., in *Pharmacol. Biochem. Behav.*, 30, 249 (1988) for an explanation of the metabolic pathways of nicotine and the formation of this metabolic product are discussed.

5-Hydroxycotinine

5-Hydroxycotinine has the molecular structure shown above;

The physiologically active form is the (−)-isomer, so as used herein, the term "5-hydroxycotinine" includes (−)-5-hydroxycotinine, or the racemic form, (+/−)-5-hydroxycotinine. The free base, depicted above, can be employed in the practice of the invention, as can the pharmaceutically acceptable salts. These include the amine-acid addition salts of nontoxic organic acids or inorganic acids, such as the tartarate, fumarate, citrate, maleate, malate, hydrobromide, hydrochloride, sulfate, phosphate and the like. Also, see P. Jacob III, et al., in *Pharmacol. Biochem. Behav.*, 30, 249 (1988) for an explanation of the metabolic pathways of nicotine and the formation of this metabolic product are discussed.

Cotinine is the major metabolite of nicotine which accumulates in the body as a result of nicotine exposure and has previously been believed to be pharmacologically inactive. For example, see N. L. Benowitz, "The use of biologic fluid samples in assessing tobacco smoke consumption", in *Measurement in the Analysis and Treatment of Smoking Behavior*, J. Grabowski et al., eds., NIDA Research Monograph No. 48, UPHS, ADAMHA (1983). In contrast to nicotine, cotinine has a relatively long terminal elimination half-life (two versus sixteen hours, respectively). Due to this pharmacological characteristic, cotinine has become the principally used objective biochemical marker of nicotine exposure in cigarette smoking and/or cessation-related research paradigms.

While cotinine is a well-known metabolite of nicotine and is routinely measured in many laboratories, no systematic investigation of the physiological and subjective effects produced by intravenous cotinine administration has been performed in humans. K. I. Yamamoto et al., *International J. Neuropharmacol.*, 4, 359 (1965), reported that intravenous cotinine produced increases in EEG activity and behavioral arousal in cats with only a slight decrease in blood pressure. In squirrel monkeys, intramuscular cotinine injections increased rates of responding on fixed interval schedules of reinforcement over a wide range of doses (M. E. Risner et al., *J. Pharmacol. Exp. Ther.*, 234, 113 (1985); S. R. Goldberg et al., *Psychopharmacology*, 97, 295 (1989)). These findings, taken together, suggest that cotinine acts as a psychomotor stimulant. However, the pharmacologic mechanism of action has yet to be determined.

In two recent human studies, the pharmacokinetic profiles of intravenous and orally administered cotinine were examined without emphasis on measuring the subjective and/or physiological changes induced by this compound (N. L. Benowitz et al., *Clin. Pharmacol. Ther.*, 34, 604 (1983); P. J. DeSchepper et al., *Eur. J. Pharmacol.*, 31, 583 (1987)). Moreover, using an uncontrolled experimental design, Benowitz et al., *Clin. Pharmacol. Ther.*, 34, 604 (1983), found that intravenous cotinine produced no cardiovascular changes and only slight differences in various subjective ratings which were comparable to placebo-induced changes found in other experiments with nicotine. Consequently, Benowitz and his colleagues concluded that cotinine lacked significant pharmacologic activity in humans.

While the most extensively studied metabolite of nicotine is cotinine, other work has examined the behavioral effects of other nicotine metabolites. In squirrel monkeys and beagle dogs, intramuscular nornicotine injections increased rates of responding on fixed interval schedules of reinforcement and was discriminated as nicotine using a discrimination procedure (M. E. Risner et al., *J. Pharmacol. Exp. Ther.*, 234, 113 (1985); S. R. Goldberg et al., *Psychopharmacology*, 97, 295 (1989)). These findings suggest that nornicotine is psychoactive. In another studying pharmacokinetics, G. Scherer et al., *Klin Wochenschr*, 66, 5 (1988), intravenously administered (−)-3-hydroxycotinine to male cigarette smokers and determined its half-life to be approximately six hours. No mention was made of toxic side effects or specific activity from the drug.

Administration and Dosages

While it is possible that, for use in therapy, nicotine metabolites and/or their salts thereof may be administered as the pure chemicals, as by inhalation of a fine powder via an insufflator, it is preferable to present the active ingredient as a pharmaceutical formulation. The invention thus further provides a pharmaceutical formulation comprising of a nicotine metabolite or combination of nicotine metabolites or their pharmaceutically acceptable salts thereof, together with one or more pharmaceutically acceptable carriers therefor and, optionally, other therapeutic and/or prophylactic ingredients. The carrier(s) must be acceptable, in the sense of being compatible with the other ingredients of the formulation and not deleterious to the recipient thereof.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; or in a chewable base such as a synthetic resin or chicle for ingestion of the cotinine from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, prefilled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, a nicotine metabolite or combination of nicotine metabolites may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279, 4,668,506 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842.

Formulations suitable for topical administration in the mouth include unit dosage forms such as lozenges comprising active ingredient in a flavored base, usually sucrose and acadia or tragacanth; pastilles comprising the active ingredient in an inert base such as gelatin and glycerin or sucrose and acacia; mucoadherent gels, and mouthwashes comprising the active ingredient in a suitable liquid carrier. When desired, the above-described formulations can be adapted to give sustained release of the active ingredient employed, e.g., by combination with certain hydrophilic polymer matrices, e.g., comprising natural gels, synthetic polymer gels or mixtures thereof.

Pharmaceutical formulations suitable for rectal preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered from an insufflator, nebulizer or a pressurized pack or other convenient means of delivering an aerosol spray.

Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intranasal administration, the compounds of the invention may be administered via a liquid spray, such as via a plastic bottle atomizer. Typical of these are the Mistometer a (Wintrop) and Medihaler (Riker).

For topical administration to the eye, the nicotine metabolite or combination of nicotine metabolites can be administered as drops, gels (see, S. Chrai et al., U.S. Pat. No. 4,255,415), gums (see S. L. Lin et al., U.S. Pat. No. 4,136,177) or via a prolonged-release ocular insert (see A. S. Michaels, U.S. Pat. No. 3,867,519 and H. M. Haddad et al., U.S. Pat. No. 3,870,791).

The pharmaceutical compositions according to the invention may also contain other adjuvants such as flavorings, colorings, antimicrobial agents, or preservatives.

It will be further appreciated that the amount of a nicotine metabolite or combination of nicotine metabolites, or their active salts or derivative thereof, required for use in treatment will vary not only with the particular salt selected but also with the route of administration, the nature of the condition being treated and the age and condition of the patient and will be ultimately at the discretion of the attending physician or clinician.

In general, however, a suitable dose will be in the range of from about 1 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day, calculated as the nicotine metabolite in the free base form.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 PM, preferably, about 1 to 50 pM, most preferably, about 2 to about 30 pM. This may be achieved, for example, by the intravenous injection of a 0.05 to 5% solution of the active ingredient, optionally in saline, or orally administered as a bolus containing about 1–100 mg of the active ingredient.

Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will be further described by reference to the following detailed Example.

EXAMPLE I

Intravenous Administration of (−)-Cotinine

A. Subjects:

Participants included 18 healthy male volunteers between the ages of 18 and 40 years old who had 1) no history of psychiatric, alcohol and drug abuse disorders, 2) smoked at least one pack of cigarettes per day for one year prior to study admission, 3) an expired-air carbon monoxide concentration of greater than 20 ppm, 4) not currently on any medication, and 5) not donated blood in the past 90 days. Potential subjects were carefully screened for physical and mental health problems.

B. Drug Preparation and Administration Procedures:

(−)-Cotinine base was synthesized from (−)-nicotine using the bromine-zinc oxidation method described by E. R. Bowman et al., *Biochem. Preparations*, 10, 36 (1963). Hereinafter, the term "cotinine" will be used to refer to (−)-cotinine. The cotinine base was analyzed for impurities using gas chromatography/mass spectrometry and thin layer chromatography and found to be pure. Using sterile techniques, cotinine solution was prepared for intravenous administration. Cotinine base was combined with sterile normal saline solution to achieve a concentration of three mg of cotinine base per one ml of solution. This solution was autoclaved and found to be non-pyrogenic using a standard pyrogenicity testing. The cotinine solution was again tested for molecular structure integrity and concentration accuracy. Next, 10 ml of cotinine solution (30 mg cotinine) were placed into 20 ml injection vials, sealed and stored in a refrigerator until used. The placebo was ten ml of sterile normal saline solution. Placebo and active drug vials were prepared and labeled in a double-blind manner by pharmacy personnel. In addition to pharmacy personnel, one study physician who had no contact with subjects during the experimental sessions had access to the drug code in the event of a medical emergency.

During sessions, subjects received 10 ml (30 mg) of cotinine base solution diluted to 15 ml with sterile normal saline solution or placebo (15 ml of sterile saline solution) infused intravenously through a 20 gauge indwelling intravenous catheter. This infusion rate was chosen so as not to exceed two mg per minute of cotinine delivered to the subject. Infusions were performed using a controlled-rate syringe infusion pump. All subjects received cotinine and placebo infusions using a randomly assigned double-blind counterbalanced-order design.

C. Dependent Measures:

The physiological parameters monitored included heart rate, systolic, diastolic and mean arterial blood pressure, and a 12-lead electrocardiogram (ECG) with measurement of PR, QRS and QT intervals. The biochemical parameters included expired-air carbon monoxide level (CO), serum nicotine and cotinine concentrations. Carbon monoxide was measured using standard techniques. The serum nicotine and cotinine concentration assays were performed using gas chromatography and mass spectrometry at the Laboratory of Physiological Hygiene at the University of Minnesota Medical School.

Self-reported ratings of subjective state, mood and cigarette withdrawal symptoms were obtained from the subjects. These measures included the Profile of Mood States questionnaire (POMS), several 100 mm visual analog scales (VAS) and the cigarette withdrawal symptoms checklist (WSC) of symptoms related to the cigarette withdrawal syndrome (J. R. Hughes et al., Arch, Gen. Psychiatry, 43, 289, (1986)). The Record of Withdrawal Symptom is a 0=(none) to 5=(severe) scale of 12 symptoms associated with TWS: craving for nicotine, irritable/angry, anxious/tense, difficulty concentrating, restless, impatient, excessive hunger, insomnia, increased eating, drowsiness, headaches and miscellaneous group including tremor, heart racing, sweating, dizzy or g.i. problems.

Two 100 mm VAS forms were used. One with 11 adjectives including "Pleasant", "Need for Cigarettes", "Energy", "Hungry", "Down", "Sedated", "Anxious", "Stimulated", "Fatigue", "Craving for Cigarettes" and a separate VAS for "Craving for Tobacco" rated form none to extremely. From the VAS forms, a measure of "Vigor" was created by subtracting the sedation score from the stimulation score. Also, an adverse effects questionnaire (AEQ) was used to assess possible problems associated with cotinine administration. These problems were restlessness, headaches, tachycardia/palpatations, tremor, excessive sweating, nausea/vomiting, upset stomach, lightheadedness/dizzy, drowsy, irritable, and excessive salivation. The symptoms assessed were those known to be experienced following nicotine administration.

D. Procedure:

This study was performed on an outpatient basis over nine days. Subjects were required to attend five scheduled laboratory sessions. All sessions were held at the Tobacco Research Laboratory associated with the University of Minnesota Hospital Complex. The first session was used for obtaining informed consent, physical and psychological screening of the prospective participants, background and baseline data collection. Also, the subject habituated to the data collection procedures utilized during the sessions. If the participant met inclusion criteria, he was scheduled for his next visit. Prior to session 2, the subject was randomly-assigned to one of the two cotinine administration order conditions.

Sessions 2 and 4 were used to collect data for all dependent variables under conditions of ad libitum cigarette smoking and serving as a baseline from which to assess tobacco withdrawal induced changes measured at the beginning of sessions 3 and 5, respectively. All sessions were scheduled to begin between 5 and 7 pm. Sessions 2 and 4 were held seven days apart and lasted approximately 15 minutes. During these sessions, vital signs, CO, WSC, VAS, POMS and AEQ were completed. Blood was drawn for later measurement of serum nicotine and cotinine concentration. At the end of sessions 2 and 4 and after departing the laboratory, subjects were required to refrain from cigarette smoking and other forms of tobacco use over the next 48 hours. At the end of this 48 hour period following sessions 2 and 4, subjects reported to the laboratory for the two drug infusion sessions 3 and 5, respectively.

During sessions 3 and 5, subjects received cotinine and placebo infusions in a counterbalanced order during these sessions. Sessions 3 and 5 were held 48 hours after sessions 2 and 4 during which time the subject was to remain tobacco abstinent. Abstinence was determined by using biochemical markers of smoke exposure including CO and serum cotinine concentrations. After the subject reported to the laboratory, baseline measurements of CO, vital signs, WSC, VAS, POMS and AEQ were made. Next, the ECG electrodes were attached to the chest wall and limbs. A 20 gauge indwelling intravenous catheter was placed in a prominent vein in the non-dominant forearm in order to allow the subject to freely complete subjective effects questionnaires during the remainder of the session. The catheter was used for intravenous drug administration and access in the event of an adverse medical event. Heart rate and blood pressure were recorded. Using standard venipuncture techniques, five mls of blood was drawn from the antecubital area of the dominant arm for later serum nicotine and cotinine concentration analyses. At intervals of 5, 15, 30, 60 and 120 minutes after the drug infusion, heart rate, blood pressure, ECG, WSC, VAS, AEQ were completed, and blood was drawn for later serum nicotine and cotinine concentration analyses. Also, the POMS was completed at 30, 60 and 120 minutes after drug administration. The blood samples were allowed to stand for 30 minutes, centrifuged for 10 minutes and the serum was pipetted into plastic cryovials for storage in a −20 degree C. freezer until the nicotine/cotinine assays were performed.

E. Statistical Analyses:

All questionnaires were scored and entered into a computer by a research assistant who was blind to the dosing conditions. At the end of the experimental period and after all data scoring, collation and entry were completed, the drug order code and serum cotinine concentrations were entered into the computer.

Of the eighteen subjects who began the study, fourteen subjects were considered to be tobacco abstinent using the biochemical markers of cigarette smoke exposure during the two abstinence periods. As a result, only the data from these fourteen individuals were included in the statistical analyses. The statistical analyses included a two within subjects factor repeated measures analysis of variance (Dose×Time) using SPSS for the microcomputer. Due to large expectancy effects which occurred at the end of the session, the two hour time point for all variables not included in the analyses. Statistical significance was defined as a p-value equal to or less than a five percent probability of a chance occurrence.

F. Results:

Eighteen male cigarette smokers who were required to be abstinent prior to receiving the drug infusions in sessions 3 and 5 participated. Upon receipt of the serum cotinine concentration data, four subjects were found not to be abstinent from cigarette smoking during the abstinence phases. Their data was excluded from subsequent statistical analyses. Of the four data sets removed, two received drug first and two received placebo first maintaining the counterbalanced-order design. The data presented herein represent those collected from the 14 study-compliant completing participants.

The participants were healthy male cigarette smokers whose average age was 25.6 years (SD=6.5). None of the participants were interested in cigarette smoking cessation. They smoked an average of 25.4 (SD=6.0) cigarettes per day. Their average expired-air carbon monoxide concentration was 9.1 (SD=7.3). Their average expressed-air carbon monoxide concentration was 28.1 ppm (SD=10.3). The average FTC estimated nicotine yield of their cigarettes was 0.87 (SD=0.3). Their average baseline serum cotinine concentration was 378 (SD=16.3). Their mean education level was 14.5 years (SD=1.7).

TABLE 1

| | Biochemical Measures | | | | |
|---|---|---|---|---|---|
| Variable | Cotinine Mean (SE) | Placebo Mean (SE) | Difference Mean (SE) | T-SCORE | P-VALUE |
| Serum Cotinine Concentration (session change) | 430 (26) | −11 (2.3) | 441 (27) | 16.4 | .001 |
| Serum Nicotine Concentration (session change) | 0.1 (0.1) | 0.0 (0.1) | 0.1 (0.2) | 0.6 | ns | ns = non-significant

The average baseline serum cotinine concentrations for the sessions were as follows (ng/ml): Session 2: 378 (SE=43) Session 3: 48 (SE=5.8); Session 4: 308 (SE=24); and Session 5: 54 (SE=6.7). The average baseline serum nicotine concentrations (ng/ml) for sessions 3 and 5 were 0.4 (SE=0.2) and 0.2 (SE=0.2), respectively. In Table 1, the sessional changes in serum cotinine and nicotine concentrations are listed. These values represent the session end minus session beginning concentrations. Serum cotinine concentration increased by 430 ng/ml of serum in the cotinine condition and decreased 11 ng/ml in the placebo condition (T(13)=16.4; p=0.001). More importantly, the serum nicotine concentration showed no change during the session which rules out the possibility of unanticipated nicotine administration as the agent responsible for the reported subjective effects in this experiment. The observed change in nicotine concentration was consistent with the limits of sensitivity of the analyses.

TABLE 2

| | SUBJECTIVE MEASURES | | | | | | | |
|---|---|---|---|---|---|---|---|---|
| Variable | 0 min Mean (SE) | 5 min Mean (SE) | 15 min Mean (SE) | 30 min Mean (SE) | 60 min Mean (SE) | Dose p-value | Time p-value | Dosex-Time p-value |
| SEDATED (VAS) | | | | | | | | |
| Cotinine | 26 (6) | 28 (6) | 27 (5) | 30 (6) | 27 (4) | .03 | .07 | ns |
| Placebo | 24 | 33 | 42 | 40 | 37 | | | |

TABLE 2-continued

| | SUBJECTIVE MEASURES | | | | | | | |
|---|---|---|---|---|---|---|---|---|
| Variable | 0 min Mean (SE) | 5 min Mean (SE) | 15 min Mean (SE) | 30 min Mean (SE) | 60 min Mean (SE) | Dose p-value | Time p-value | Dosex-Time p-value |
| | (3) | (5) | (7) | (7) | (7) | | | |
| RESTLESS (WSC) | | | | | | | | |
| Cotinine | 3.1 (.3) | 1.4 (.3) | 1.4 (.3) | 1.6 (.4) | 1.8 (.4) | .05 | ns | ns |
| Placebo | 2.6 (.4) | 0.9 (.2) | 0.9 (.2) | 0.9 (.2) | 0.9 (.3) | | | |
| RESTLESS-NESS (AEQ) | | | | | | | | |
| Cotinine | 1.8 (.2) | 1.2 (.1) | 1.2 (.1) | 1.4 (.1) | 1.4 (.2) | .05 | .001 | ns |
| Placebo | 1.9 (.2) | 1.0 (.0) | 1.0 (.0) | 1.1 (.1) | 1.0 (.0) | | | |
| INSOMNIA (WSC) | | | | | | | | |
| Cotinine | 1.2 (.3) | 0.1 (.1) | 0.1 (.1) | 0.1 (.1) | 0.1 (.1) | .02 | .01 | .02 |
| Placebo | 0.6 (.3) | 0.1 (.1) | 0.0 (0) | 0.0 (0) | 0.0 (0) | | | |
| VIGOR (VAS) | | | | | | | | |
| Cotinine | 16 (9) | 13 (6) | 11 (5) | 7 (5) | 7 (7) | .05 | .01 | ns |
| Placebo | 28 (6) | 9 (10) | −6 (7) | −3 (8) | −9 (6) | | | |
| PLEASANT (VAS) | | | | | | | | |
| Cotinine | 41 (3) | 49 (4) | 46 (4) | 45 (5) | 44 (5) | .05 | .05 | ns |
| Placebo | 44 (3) | 53 (3) | 55 (4) | 50 (4) | 51 (4) | | | |
| ANXIOUS/ TENSE (WSC) | | | | | | | | |
| Cotinine | 3.2 (.4) | 2.1 (.4) | 1.8 (.3) | 1.7 (.3) | 2.1 (.4) | .05 | ns | ns |
| Placebo | 2.9 (.4) | 1.1 (.2) | 1.3 (.3) | 1.2 (.2) | 1.0 (.2) | | | |
| TENSION/ ANXIETY (POMS) | | | | | | | | |
| Cotinine | 17 (2) | | | 10 (1) | 10 (2) | .05 | .001 | ns |
| Placebo | 14 (2) | | | 6 (1) | 6 (1) | | | | ns = non-significant

Intravenous cotinine base administration compared to placebo had no effect on heart rate, blood pressure or the ECG intervals (e.g., PR, QRS and QT). In Table 2, the subjective ratings of mood and cigarette withdrawal symptoms are listed. Throughout the study, subjects rated themselves as feeling less pleasant (p=0.05) and sedated (P=0.03), while simultaneously reporting feeling increased vigor (p=0.05), anxious/tense (p=0.05), tension/anxiety (p=0.05), restless (p 0.05), restlessness (p=0.05) and insomnia (p=0.02) as function of cotinine administration. The feelings of tension/anxiety and restlessness were rated on different instruments showing some degree of reliability for these measures.

The statistical analyses performed on the various measures of craving using data from both experimental sessions yielded no significant differences. This was likely due to immense variability generated by the subjects in the third session. Therefore, to examine the effects of cotinine on craving, a reanalysis of the data comparing cotinine versus placebo on the maximum sessional decrease from baseline for the various craving measures was performed using only session 5 data. The results are summarized in Table 3. The "Craving for Tobacco" visual analog score (p=0.02) and the average of all craving scales (p=0.05) were significantly decreased in the cotinine condition as compared to placebo. The average of all craving scores was achieved using the WSC "craving for nicotine" score multiplied by 20 and then adding all of the scores and dividing this total by four. There was a consistent directional effect across all measures with the cotinine showing a greater influence than placebo.

TABLE 3

Maximum Craving Decrease Scores

| Variable | Cotinine Mean (SE) | Placebo Mean (SE) | Difference Mean (SE) | T-SCORE | P-VALUE |
|---|---|---|---|---|---|
| Need for Cigarettes (VAS-1) | −24.8 (6.3) | −13.7 (2.7) | −11.1 (6.8) | −1.63 | 0.07 |
| Craving for Cigarettes (VAS-1) | −19.6 (4.7) | −16.3 (2.7) | −3.3 (5.5) | −0.59 | ns |
| Craving for Tobacco (VAS-2) | −25.6 (3.8) | −14.3 (3.1) | −11.3 (4.8) | −2.33 | 0.02 |
| Craving for Nicotine (WSC) | −1.56 (.18) | −1.11 (.26) | −0.45 (.32) | −1.41 | 0.09 |
| Average of All Craving Scales (VAS-1,-2,WSC) | −24.9 (2.8) | −17.4 (3.2) | −7.5 (4.2) | −1.77 | 0.05 | ns = non-significant

In Table 4, various measures of appetite are presented. The repeated measures analysis of variance showed a trend towards significance, however it was not significant. 14 of 18 participants showed a minimal to large effect with cotinine decreasing self-reported ratings of hunger (Sign test; $p<0.05$). As a result, a two within subject factor repeated measures analysis of variance was performed on these 14 individuals. The subjects reported feeling significantly less hungry during the cotinine session when compared to placebo ($p<0.001$). While no significant difference was found for ratings of excessive hunger, there was a similar trend in these individuals. No difference was observed for increased eating. The average hunger score was derived by using the weighted average of excessive hunger (excessive hunger×20) added to the rating of hungry. The average hunger rating was significantly decreased in the cotinine condition as opposed to placebo ($p<0.02$).

TABLE 4

HUNGER SCORES

| Variable | 0 min Mean (SE) | 5 min Mean (SE) | 15 min Mean (SE) | 30 min Mean (SE) | 60 min Mean (SE) | Dose p-value | Time p-value | Dose×Time p-value |
|---|---|---|---|---|---|---|---|---|
| HUNGRY | | | | | | | | |
| Cotinine | 34 (5) | 27 (5) | 21 (3) | 26 (5) | 35 (6) | .001 | .06 | ns |
| Placebo | 42 (6) | 36 (6) | 41 (6) | 39 (6) | 43 (6) | | | |
| EXCESSIVE HUNGER | | | | | | | | |
| Cotinine | 0.8 (.2) | 0.3 (.1) | 0.5 (.2) | 0.6 (.2) | 1.0 (.3) | ns | .03 | ns |
| Placebo | 1.2 (.4) | 0.7 (.3) | 0.6 (.3) | 0.9 (.4) | 1.2 (.4) | | | |
| INCREASED EATING | | | | | | | | |
| Cotinine | 1.4 (.3) | 0.2 (.1) | 0.2 (.2) | 0.3 (.2) | 0.3 (.2) | ns | .001 | ns |
| Placebo | 1.1 (.4) | 0.2 (.1) | 0.2 (.1) | 0.1 (.1) | 0.2 (.1) | | | |
| TOTAL HUNGER SCORE | | | | | | | | |
| Cotinine | 47 (9) | 33 (6) | 31 (7) | 39 (9) | 55 (11) | .02 | .007 | ns |
| Placebo | 67 (11) | 50 (10) | 54 (10) | 57 (13) | 67 (13) | | | | ns = non-significant

G. Discussion:

The purpose of the study was to determine whether an intravenously administered nicotine metabolite (cotinine base) has significant psychoactivity in abstinent tobacco users. The data presented herein is the first demonstration that a nicotine metabolite is pharmacologically-active and produces many subjective changes in humans without affecting cardiovascular activity. Further, while cotinine administration appeared to exacerbate certain symptoms of the tobacco withdrawal syndrome including restlessness and anxiety/tension, it simultaneously attenuated other withdrawal symptoms including sedation and the various craving measures (for tobacco, nicotine and cigarettes) experienced during the session. Also, the subjective profile of cotinine base following intravenous administration is consistent with the activity of a psychomotor stimulant.

Other findings reported herein suggest that a nicotine metabolite, cotinine, may serve to act as an appetite suppressant and could be responsible in part for the decreased body weight of tobacco users. The data suggest that cotinine is a psychomotor stimulant and its ability to suppress appetite probably stems from this activity. Acutely, people using psychomotor stimulants typically report more anxiety, tension, insomnia, irritability, restlessness and less sedated until they become tolerant to these effects. Also, psychomotor stimulants typically are used as appetite suppressants (e.g., phentermine, phenmetrazine, amphetamine, fenfluramine, diethylproprion). Nicotine has been shown to increase resting metabolism and decrease perceived taste intensity of various foods in nicotine-experienced and nicotine-naive individuals suggesting a mechanism by which this drug exerts its effects. If nicotine and its metabolites act through the same mechanism, then they should act similarly in nicotine-experienced, nicotine-abstinent or nicotine-naive individuals.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

I claim:

1. A therapeutic method to alleviate the tobacco withdrawal syndrome in a human comprising: administering an amount of a nicotine metabolite or combination of nicotine metabolites or their pharmaceutically acceptable salts thereof to a human in need of such treatment, in an amount in the range of 1 to 100 milligrams per kilogram of body weight of the human per day calculated as the nicotine metabolite or combination of nicotine metabolites in the free base form that is effective to reduce or eliminate symptoms of tobacco withdrawal syndrome.

2. The method of claim 1 wherein: the nicotine metabolite is (−)-cotinine, (−)-norcotinine, (−)-nornicotine, (−)-nicotine N-oxide, (−)-cotinine N-oxide, (−)-3-hydroxycotinine or (−)-5-hydroxycotinine.

3. The method of claim 1 wherein: the nicotine metabolite or the pharmaceutically acceptable salt thereof is administered orally.

4. The method of claim 1 wherein: the nicotine metabolite or the pharmaceutically acceptable salt thereof is orally administered by means of a chewing gum.

5. The method of claim 1 wherein: the nicotine metabolite or the pharmaceutically acceptable salt thereof is administered parenterally.

6. The method of claim 1 wherein: the nicotine metabolite or the pharmaceutically acceptable salt thereof is administered intraocularly.

7. The method of claim 1 wherein: the nicotine metabolite or the pharmaceutically acceptable salt thereof is administered via an intraocular insert.

8. The method of claim 1 wherein: the nicotine metabolite or the pharmaceutically acceptable salt thereof is administered intravenously.

9. The method of claim 1 wherein: the nicotine metabolite or the pharmaceutically acceptable salt thereof is administered intranasally.

10. A therapeutic method to alleviate the symptoms of nicotine withdrawal in a human comprising: administering an amount of nicotine metabolite or combination of nicotine metabolites or their pharmaceutically acceptable salts thereof to a human in need of such treatment, in an amount in the range of 1 to 100 milligrams per kilogram of body weight of the human per day calculated as the nicotine metabolite or combination of nicotine metabolites in the free base form that is effective to reduce or eliminate symptoms of nicotine withdrawal.

11. The method of claim 10 wherein: the nicotine metabolite is (−)-cotinine, (−)-norcotinine, (−)-nornicotine, (−)-nicotine N-oxide, (−)-cotinine N-oxide, (−)-3-hydroxycotinine or (−)-5-hydroxycotinine.

12. The method of claim 10 wherein: the nicotine metabolite or the pharmaceutically acceptable salt thereof is administered orally.

13. The method of claim 10 wherein: the nicotine metabolite or the pharmaceutically acceptable salt thereof is orally administered by means of a chewing gum.

14. The method of claim 10 wherein: the nicotine metabolite or the pharmaceutically acceptable salt thereof is administered parenterally.

15. The method of claim 10 wherein: the nicotine metabolite or the pharmaceutically acceptable salt thereof is administered intraocularly.

16. The method of claim 10 wherein: the nicotine metabolite or the pharmaceutically acceptable salt thereof is administered via an intraocular insert.

17. The method of claim 10 wherein: the nicotine metabolite or the pharmaceutically acceptable salt thereof is administered intravenously.

18. The method of claim 10 wherein: the nicotine metabolite or the pharmaceutically acceptable salt thereof is administered intranasally.

19. A therapeutic method to alleviate the craving associated with cessation of tobacco use in a human comprising: administering an amount of a nicotine metabolite or combination of nicotine metabolites or their pharmaceutically acceptable salts thereof, to a human in need of such treatment, in an amount in the range of 1 to 100 milligrams per kilogram of body weight of the human per day calculated as the nicotine metabolite or combination of nicotine metabolites in the free base form that is effective to alleviate craving for tobacco.

20. The method of claim 19 wherein: the nicotine metabolite is (−)-cotinine, (−)-norcotinine, (−)-nornicotine, (−)-nicotine N-oxide, (−)-cotinine N-oxide, (−)-3-hydroxycotinine or (−)-5-hydroxycotinine.

21. The method of claim 19 wherein: the nicotine metabolite or the pharmaceutically acceptable salt thereof is administered orally.

22. The method of claim 19 wherein: the nicotine metabolite or the pharmaceutically acceptable salt thereof is orally administered by means of a chewing gum.

23. The method of claim 19 wherein: the nicotine metabolite or the pharmaceutically acceptable salt thereof is administered parenterally.

24. The method of claim 19 wherein: the nicotine metabolite or the pharmaceutically acceptable salt thereof is administered intraocularly.

25. The method of claim 19 wherein: the nicotine metabolite or the pharmaceutically acceptable salt thereof is administered via an intraocular insert.

26. The method of claim 19 wherein: the nicotine metabolite or the pharmaceutically acceptable salt thereof is administered intravenously.

27. The method of claim 19 wherein: the nicotine metabolite or the pharmaceutically acceptable salt thereof is administered intranasally.

28. An article of manufacture comprising packaging material and a unit dosage form of a pharmaceutical agent contained within said packaging material, wherein: said pharmaceutical agent comprises a nicotine metabolite or combination of nicotine metabolites or their pharmaceutically acceptable salts thereof in an amount effective to alleviate tobacco withdrawal syndrome, symptoms of nicotine withdrawal and wherein said packaging material includes instruction means which indicate that said nicotine metabolite or combination of nicotine metabolites or said pharmaceutically acceptable salts thereof can be used by a person in the range of 1 to 100 milligrams per kilogram of body weight of the person per day calculated as the nicotine metabolite or combination of nicotine metabolites in the free base form for alleviating (a) symptoms of tobacco withdrawal syndrome, (b) symptoms of nicotine withdrawal, and (c) the craving associated with the cessation of nicotine use.

29. The article of manufacture of claim 28 wherein: the unit dosage form is a tablet or capsule.

30. The article of manufacture of claim 28 wherein: the unit dosage form is a chewing gum.

31. The article of manufacture of claim 28 wherein: the unit dosage form is an intraocular insert.

32. The article of manufacture of claim 28 wherein: the unit dosage form is an aqueous solution of nicotine metabolite or a pharmaceutically acceptable salt thereof.

33. The article of manufacture of claim 28 wherein: the instruction means is a label or tag attached to said packaging.

34. The article of manufacture of claim 28 wherein: the instruction means is a printed package insert.

35. A therapeutic method to alleviate tobacco withdrawal syndrome in a human comprising: administering an amount of a combination of (−)-cotinine and (−)-norcotinine or their pharmaceutically acceptable salts thereof to a human in need of such treatment in an amount in the range of 1 to 100 milligrams per kilogram of body weight of the human per day calculated as the combination of (−)-cotinine and (−)-norcotinine in the free base form which is effective to reduce or eliminate symptoms of tobacco withdrawal syndrome.

36. The method of claim 35 wherein: the combination of (−)-cotinine and (−)-norcotinine or the pharmaceutically acceptable salts thereof is administered orally.

37. The method of claim 35 wherein: the combination of (−)-cotinine and (−)-norcotinine or the pharmaceutically acceptable salts thereof is administered by means of a chewing gum.

38. The method of claim 35 wherein: the combination of (−)-cotinine and (−)-norcotinine or the pharmaceutically acceptable salts thereof is administered parenterally.

39. The method of claim 35 wherein: the combination of (−)-cotinine and (−)-norcotinine or the pharmaceutically acceptable salts thereof is administered intraocularly.

40. The method of claim 35 wherein: the combination of (−)-cotinine and (−)-norcotinine or the pharmaceutically acceptable salts thereof is administered via an intraocular insert.

41. The method of claim 35 wherein: the combination of (−)-cotinine and (−)-norcotinine or the pharmaceutically acceptable salts thereof is administered intravenously.

42. The method of claim 35 wherein: the combination of (−)-cotinine and (−)-norcotinine or the pharmaceutically acceptable salts thereof is administered intranasally.

43. A therapeutic method to alleviate tobacco withdrawal syndrome in a human comprising: administering an amount of a combination of (−)-cotinine and (−)-nornicotine or their pharmaceutically acceptable salts thereof to a human in need of such treatment in an amount in the range of 1 to 100 milligrams per kilogram of body weight of the human per day calculated as the combination of (−)-cotinine and (−)-nornicotine which is effective to reduce or eliminate symptoms of tobacco withdrawal syndrome.

44. The method of claim 43 wherein: the combination of (−)-cotinine and (−)-nornicotine or the pharmaceutically acceptable salts thereof is administered orally.

45. The method of claim 43 wherein: the combination of (−)-cotinine and (−)-nornicotine or the pharmaceutically acceptable salts thereof is orally administered by means of a chewing gum.

46. The method of claim 43 wherein: the combination of (−)-cotinine and (−)-nornicotine or the pharmaceutically acceptable salts thereof is administered parenterally.

47. The method of claim 43 wherein: the combination of (−)-cotinine and (−)-nornicotine or the pharmaceutically acceptable salts thereof is administered intraocularly.

48. The method of claim 43 wherein: the combination of (−)-cotinine and (−)-nornicotine or the pharmaceutically acceptable salts thereof is administered via an intraocular insert.

49. The method of claim 43 wherein: the combination of (−)-cotinine and (−)-nornicotine or the pharmaceutically acceptable salts thereof is administered intravenously.

50. The method of claim 43 wherein: the combination of (−)-cotinine and (−)-nornicotine or the pharmaceutically acceptable salts thereof is administered intranasally.

51. A therapeutic method to alleviate the craving associated with cessation of nicotine use in a human comprising: administering an amount of a nicotine metabolite or combination of nicotine metabolites or their pharmaceutically acceptable salts thereof to a human in need of such treatment in an amount in the range of 1 to 100 milligrams per kilogram of body weight of the human per day calculated as the nicotine metabolite or combination of nicotine metabolites in the free base form that is effective to alleviate craving for nicotine.

52. The method of claim 51 wherein: the nicotine metabolite is (−)-cotinine, (−)-norcotinine, (−)-nornicotine, (−)-nicotine N-oxide, (−)-cotinine N-oxide, (−)-3-hydroxycotinine or (−)-5-hydroxycotinine.

53. The method of claim 51 wherein: the nicotine metabolite or combination of nicotine metabolites or the pharmaceutically acceptable salts thereof is administered orally.

54. The method of claim 51 wherein: the nicotine metabolite or combination of nicotine metabolites or the pharmaceutically acceptable salts thereof is orally administered by means of a chewing gum.

55. The method of claim 51 wherein: the nicotine metabolite or combination of nicotine metabolites or the pharmaceutically acceptable salts thereof is administered orally.

56. The method of claim 51 wherein: the nicotine metabolite or combination of nicotine metabolites or the pharmaceutically acceptable salts thereof is administered intraocularly.

57. The method of claim 51 wherein: the nicotine metabolite or combination of nicotine metabolites or the pharmaceutically acceptable salts thereof is administered via an intraocular insert.

58. The method of claim 51 wherein: the nicotine metabolite or combination of nicotine metabolites or the pharmaceutically acceptable salts thereof is administered intravenously.

59. The method of claim 51 wherein: the nicotine metabolite or combination of nicotine metabolites or the pharmaceutically acceptable salts thereof is administered intranasally.

* * * * *